United States Patent [19]

Giede et al.

[11] Patent Number: 4,795,632
[45] Date of Patent: Jan. 3, 1989

[54] PREPARATIONS FOR WASHING AND RINSING HAIR

[75] Inventors: Karl Giede, Hilden; Horst Hoeffkes, Duesseldorf, both of Fed. Rep. of Germany

[73] Assignee: Henkel Kommanditgesellschaft auf Aktien, Duesseldorf, Fed. Rep. of Germany

[21] Appl. No.: 874,874

[22] Filed: Jun. 16, 1986

Related U.S. Application Data

[63] Continuation of Ser. No. 628,926, Jul. 9, 1984, abandoned.

[30] Foreign Application Priority Data

Jul. 21, 1983 [DE] Fed. Rep. of Germany ....... 3326230

[51] Int. Cl.$^4$ .......................... A61K 7/06; A61K 7/08; C08F 16/34
[52] U.S. Cl. ................... 424/70; 424/DIG. 4; 424/74; 514/852; 514/864; 526/315; 562/578
[58] Field of Search .................. 424/70; 562/578; 526/315

[56] References Cited

U.S. PATENT DOCUMENTS

| | | | |
|---|---|---|---|
| 2,957,931 | 7/1976 | Kennerley | 424/10 |
| 3,969,500 | 7/1976 | Kennerley | 424/10 |
| 4,128,634 | 12/1978 | Hase | 424/81 |
| 4,381,259 | 4/1983 | Homma et al. | 252/542 |

FOREIGN PATENT DOCUMENTS

| | | | |
|---|---|---|---|
| 1126750 | 6/1982 | Canada | 424/70 |
| 8410827 | 8/1986 | European Pat. Off. | 424/70 |
| 1165204 | 3/1964 | Fed. Rep. of Germany | 424/70 |
| 1617691 | 10/1970 | Fed. Rep. of Germany | 424/70 |
| 2044601 | 3/1972 | Fed. Rep. of Germany | 424/70 |
| 2452031 | 5/1976 | Fed. Rep. of Germany | 424/70 |
| 2452032 | 5/1976 | Fed. Rep. of Germany | 424/70 |
| 0015912 | 2/1979 | Japan | 424/70 |
| 0076810 | 6/1980 | Japan | 424/70 |
| 0120507 | 9/1980 | Japan | 424/70 |
| 0145995 | 11/1981 | Japan | 424/70 |
| 2027047 | 2/1980 | United Kingdom | 424/70 |
| 2028133 | 3/1980 | United Kingdom | 424/70 |

OTHER PUBLICATIONS

Chemical Abstracts, 1979, vol. 91, pp. 216667z, Nakaju.
Chemical Abstracts, 1982, vol. 96, pp. 164567y, Deguchi.
W. Fossek, Monatshefte fuer Chemie, vol. 7 (1886), pp. 20–39.
G. M. Kosolapoff, Journal of the American Chemical Soc. (1975), pp. 1500–1501.
B. Blaser, et al., Zeitschrift fuer anorganische and allgemeine Chemie, vol. 381, (1971), pp. 247–259.
W. Pöger, et al., Zeitschrift fuer anorganische and allgemeine Chemie, vol. 389 (1972), pp. 119–128.

*Primary Examiner*—Dale R. Ore
*Attorney, Agent, or Firm*—Ernest G. Szoke; Henry E. Millson, Jr.; Real J. Grandmaison

[57] ABSTRACT

Preparations for washing or rinsing hair contain polyaldehydocarboxylic acids having an average molecular weight of from 600 to 10,000, a carboxyl group content of from 5 to 9 and preferably from 7 to 9 and an aldehyde group content of from 1 to 5 and preferably from 1 to 3 per 10 monomer units, or water-soluble salts thereof. These additives reduce the smoothness of dry hair and improve body and stylability after washing. The polyaldehydocarboxylic acids are preferably used in conjunction with hair-conditioning linear alkyl and/or alkylether phosphate salts, alkyl, hydroxyalkyl and/or aminoalkyl phosphonate salts. Preferred embodiments are hair shampoos containing from about 1 to about 10% by weight of the polyaldehydocarboxylic acids and from about 5 to about 50% by weight of anionic surfactants of the alkyl sulfate and/or alkylether sulfate type and hair rinses containing from about 1 to about 10% by weight of hair-conditioning alkyl and/or alkylether phosphate salts and/or alkane phosphonate salts.

10 Claims, No Drawings

PREPARATIONS FOR WASHING AND RINSING HAIR

This application is a continuation of application Ser. No. 628,926, filed July 9, 1984, now abandoned.

BACKGROUND OF THE INVENTION

This invention relates to preparations for washing or rinsing hair, i.e. for example shampoos and after-treatment rinses, containing an additive which improves the body and combability of hair.

After washing, the hair of the head is often in a cosmetically unsatisfactory condition. It feels dull, is difficult to comb when wet and, when dry, tends to develop a static charge, which also makes combing difficult and spoils the set of the combed hair.

Accordingly, it is known that conditioning preparations, generally containing cationic surfactants, may be applied to hair after washing or shampooing or conditioning agents may be added to the hair-washing preparations to obtain a certain conditioning effect when the hair is washed. Examples of conditioning agents are, for example, water-soluble proteins, protein degradation products and polycationic polymers, for example cationic cellulose derivatives.

Whereas known auxiliaries provide for a satisfactory improvement in wet combability while cationic surfactants, for example, even though they enable antistatic charging to be reduced, the excessive smoothing of the dry hair which is almost always obtained at the same time is a considerable disadvantage because its effect is that the hair lacks body and is not receptive to styling. The smoothness of the hair is more pronounced, the lower the resistance of the dry hair to combing.

Accordingly, there is a need to find hair shampoos and rinses which considerably reduce the smoothness of dry hair without introducing any tackiness and without excessively reducing wet combability.

It is known from German application No. 24 10 283 that polymers of acrylic acid, methacrylic acid, crotonic acid, itaconic acid, and maleic acid and also copolymers thereof with a monoethylenically unsaturated monomer, particularly ethylene, vinylbenzene, vinylacetate, vinylmethylether and acrylamide, can be added to hair shampoos. However, these products reduce the resistance to combing of dry hair, i.e. they do not achieve the object of the present invention.

DESCRIPTION OF THE INVENTION

It has now been found that preparations for washing or rinsing hair in the form of an aqueous composition containing polyaldehydocarboxylic acids having an average molecular weight of from about 600 to about 10,000, a carboxyl group content of from 5 to 9 and preferably from 7 to 9 and an aldehyde group content of from 1 to 5 and preferably from 1 to 3 per 10 monomer units, or non-toxic water-soluble addition salts thereof, such as alkali metal, ammonium, mono-, di, or triethanolamine, reduce the smoothness of dry hair without significantly affecting its wet combability.

It has also been found that the wet combability of hair can be improved and, at the same time, the smoothness of dry hair reduced if preparations for washing or rinsing hair contain:
 (a) from about 0.1 to about 10% by weight of at least one of the polyaldehydocarboxylic acids described above, and one or both of the following:
 (b) from about 0.1 to about 10% by weight of an anionic hair-conditioning component selected from one or more compounds corresponding to the general formulae:

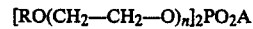

in which R is a linear alkyl group containing from 8 to 18 carbon atoms; X is hydrogen, an —OH group or an —NH$_2$ group; A is an alkali metal, ammonium, mono-, di- or triethanolammonium cation; and n is 0 or an integer of from 1 to 12; and
 (c) from about 5 to about 50% by weight of an anionic surfactant component selected from one or more compounds corresponding to the general formulae:

wherein R, A, and n have the same meanings as in component (b) above.

The polyaldehydocarboxylic acids present in the preparations of the invention as component (a) above contain monomer units corresponding to the following general formulae:

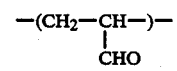      I

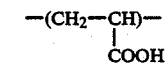      II where the units containing aldehyde and carboxylate groups can be arranged in any order. As stated above, the average molecular weight of the polyaldehydocarboxylic acids should be between about 600 and about 10,000, corresponding to an average degree of polymerization of from about 10 to about 140. The ratio of aldehyde groups to carboxyl groups should amount to between 5:5 and 1:9, i.e. from 5 to 9 carboxyl groups and correspondingly from 5 to 1 aldehyde groups should be present per 10 monomer units.

Preferred polyaldehydocarboxylic acids contain from 7 to 9 carboxyl groups and correspondingly from 3 to 1 aldehyde groups per 10 monomer units. Polyaldehydocarboxylic acids such as these are known commercially available products. They are obtained, for example, by the oxidative homopolymerization of acrolein or by the oxidative copolymerization of acrolein and acrylic acid. Commercially available polyaldehydocarboxylic acids are, for example, the following DEGUSSA Company (Frankfurt, Federal Republic of Germany) products:

POC-HS-0010, a 50% aqueous solution of a polyaldehydocarboxylic acid, average molecular weight 700, acid number 550, acid equivalent weight 102, POC-HS-2020, a 50% aqueous solution of a polyaldehydocarboxylic acid, average molecular weight 1400, acid number 585, acid equivalent weight 96, POC-HS-5060, a 40% aqueous solution of a polyaldehydocarboxylic acid, average molecular weight 4000, acid number 645, acid equivalent weight 87, POC-HS-65120, a 35% aqueous solution of a polyaldehydocarboxylic acid, average molecular weight 8500, acid number 695, acid equivalent weight 81.

The anionic, surface-active, hair-conditioning components corresponding to the general formulae $RO(CH_2-CH_2-O)_nPO_3A_2$ and $[RO(CH_2-CH_2O)_n-]_2-PO_2A$ (see component (b) above) which are useful as an optional but preferred additive to the preparations of the invention, are salts of phosphoric acid mono- and diesters of linear $C_8-C_{18}$-alkanols and of adducts of 1 to 12 moles of ethylene oxide with linear $C_8-C_{18}$-alkanols. Products such as these are obtained by reacting the alkanols or the ethylene oxide/alkanol adducts with phosphorus pentoxide, followed by neutralization with aqueous alkali hydroxides, ammonia or alkanolamines.

The anionic, surface-active $C_8-C_{18}$-alkane-1-phosphonic acids and their salts are known or can be obtained by processes known from the literature. According to U.S. Pat. No. 2,957,931, for example, they can be obtained by the radical addition of esters of phosphorous acid onto olefins, followed by hydrolysis of the alkane-1-phosphonic acid esters.

1-hydroxyalkane-1-phosphonic acids can be obtained, for example, by reacting aldehydes with $PCl_3$ using the process described by W. Fossek in Monatshefte fuer Chemie, Vol. 7 (1886), pages 20 to 39.

Alkane-1,1-diphosphonic acids can be obtained, for example, by alkylating methane diphosphonic acid using the process described by G. M. Kosolapoff in J. Am. Chem. Soc. 75 (1975), pages 1500–1501, for pentane-1,1-diphosphonic acid.

1-hydroxyalkane-1,1-diphosphonic acids can be obtained from carboxylic acids, water and $PCl_3$ by the processes described by B. Blaser et al. in Zeitschrift fuer anorganische und allgemeine Chemie, Vol. 381 (1971), pages 247–259.

1-aminoalkane-1,1-diphosphonic acids can be produced by a process described by W. Polger et al. in Zeitschrift fuer anorganische und allgemeine Chemie, Vol. 389 (1972), pages 119–128.

Preferred anionic, surface-active hair-conditioning components are $C_8-C_{18}$-alkane-1-phosphonic acids, especially the commercially available octane-1-phosphonic acid and its sodium salt.

Hair-washing preparations of the invention suitable for use as shampoos advantageously contain from about 1 to about 10% by weight of the polyaldehydocarboxylic acids (component (a) above) and from about 5 to about 50% by weight of one or more anionic surfactants selected from compounds corresponding to the general formulae $R-SO_3A$ and $RO(CH_2-CH_2O)_n-SO_3A$, in which R is a linear alkyl group containing from 8 to 18 carbon atoms, A is an alkali metal, ammonium, mono-, di- or triethanolammonium cation and n is 0 or an integer of from 1 to 12 (component (c) above).

Suitable anionic surfactants (component (c)) are, for example, the sodium salts of alkane sulfonates containing from 12 to 18 carbon atoms, the ammonium or mono-, di- or trialkanolammonium (preferably ethanolammonium) salts of alkyl sulfates based on linear or slightly branched fatty alcohols containing from 12 to 16 carbon atoms and the sodium, ammonium, mono-, di- or triethanolammonium salts of alkyl (poly) glycol ether sulfates containing from 12 to 16 carbon atoms in the alkyl group and from 1 to 6 glycol ether groups.

It is of particular advantage to use a mixture of from about 5 to about 20% by weight of an anionic surfactant of the $C_{12}-C_{16}$-fatty alcohol (poly) glycol ether sulfate type containing from 1 to 6 glycol ether groups and from about 1 to about 10% by weight of an ampholytic surfactant, a betaine surfactant or an amine oxide surfactant, based on the shampoo as a whole.

Ampholytic surfactants are, for example, $N-C_8-C_{18}$-alkyl-$\beta$-aminopropionic acids, $N-C_8-C_{18}$-alkyl-$\beta$-iminodipropionic acids or N-hydroxyethyl-N-cocoalkylamidopropyl glycine. Betaine surfactants are, for example, N-cocoalkyl dimethyl glycine and N-cocoalkylamidopropyl dimethyl glycine. Amine oxide surfactants are, for example, N-cocoalkylamidopropyl dimethyl amine oxide or N-cocoalkyl di-(2-hydroxy)-ethylamine oxide.

In addition, the hair-washing preparations of the invention can contain standard additives and formulation aids such as, for example, thickeners with foam stabilizers of the fatty acid alkanolamide type, opacifiers, for example of the ethylene glycol distearate type, pH-stabilizers and buffer systems, such as alkali or ammonium phosphates or citrates, preservatives such as formaldehyde or p-hydroxybenzoic acid esters, dyes, perfumes and known hair-cosmetic active principles, such as anti-dandruff agents or sebostatic agents.

Hair-rinsing preparations of the invention which are suitable for use as conditioning aftertreatments, for example in the form of hair rinse medicated preparations, preferably contain from about 0.1 to about 10% by weight of the polyaldehydocarboxylic acids (component (a)) and from about 1 to about 10% by weight of the anionic, hair-conditioning component (b).

Water-soluble salts of phosphoric acid mono- and diesters of linear $C_{12}-C_{18}$-fatty alcohols and of $C_8-C_{18}$-alkane-1-phosphonic acids are preferably used as component (b) when present in the preparations of the invention. A particularly suitable alkane-1-phosphonate is the sodium salt of octane-1-phosphonic acid.

In addition, the hair rinses according to the invention can contain standard additives and formulation aids such as, for example, thickeners of the water-soluble anionic or nonionic cellulose starch or guar derivative type, alginates, water-soluble thickening synthetic polymers such as, for example, polyvinyl alcohol, polyvinyl pyrrolidone, polyacrylates, polyacrylamides etc. It is preferred to use from about 1 to about 5% by weight of a water-soluble, nonionic cellulose derivative, particularly hydroxyethyl cellulose, for thickening the hair rinses of the invention. To acquire a creamy structure, they can contain aqueous dispersions or emulsions of fatty alcohols and/or cosmetic oil components and also the emulsifiers required for preparing such dispersions. In addition, the hair rinses can contain preservatives, perfumes, dyes and known hair-cosmetic active principles, such as herb extracts, vitamins, balsams, antidandruff agents or sebostatic agents.

The invention is illustrated but not limited by the following Examples.

EXAMPLES

1. Influencing wet and dry combability

A standard shampoo with and without an addition of various polyaldehydocarboxylic acids and also a pure alkylether sulfate surfactant were comparatively tested for wet combability and dry combability.

| Test shampoo formulations | A | B | C | D | E |
|---|---|---|---|---|---|
| | \multicolumn{5}{c}{% by weight} | | | | |
| $C_{12/14}$-fatty alcohol + 2 EO-sulfate-Na—salt, 28% by weight (Texapon ® N 25) | 50 | 50 | 50 | 50 | 50 |
| N—cocoalkylamidopropyl dimethyl glycine, 30% by weight (Dehyton ® K) | — | 5 | 5 | 5 | 5 |
| Wool fat alcohol ethoxylate | — | 1 | 1 | 1 | 1 |
| Ethylene glycol stearate | — | 2 | 2 | 2 | 2 |
| Perfume oil | — | 0.5 | 0.5 | 0.5 | 0.5 |
| Ammonia solution to pH 5 | — | — | 0.5 | 0.5 | 0.5 |
| POC-HS-2020 (50% by weight) | — | — | 2.0 | — | — |
| POC-HS-5060 (40% by weight) | — | — | — | 3.3 | — |
| POC-HS-65120 (35% by weight) | — | — | — | — | 3.3 |
| Water | 50 | 41.5 | 39 | 37.7 | 37.7 |
| % WC | 100 | 129 | 125 | 134 | 165 |
| % DC | 100 | 106 | 155 | 127 | 138 |

1.1 Determination of wet combability (WC) and dry combability (DC)

Dark brown, undamaged European hair locks weighing 0.7 g were cleaned for 5 minutes at 30° C. with solution A, subsequently washed free from surfactant with water at 30° C. and then treated twice for 15 minutes with tap water at 22° C. in an ultrasonic bath. The hair locks thus preconditioned were treated for 5 minutes at 30° C. with test shampoo formulations A–E, thoroughly rinsed with lukewarm water (30° C.) and then straightened out while still wet, after which excess water was stripped off and the hairs subsequently dried in a stream of dry air (16 hours/40° C.).

(a) Dry combability (DC)
To test dry combability, the locks of hair were conditioned for 16 hours at 25° C./60% relative air humidity.

(b) Wet combability (WC)
To test wet combability, the locks of hair were moistened with 50% of their weight of water.

The resistance to combing, i.e. the force required to draw a comb through a lock of hair, was then measured. To reduce the measurement error range, combing resistance was determined by combing three different locks of hair 5 times for each formulation. The averages of the work integrals obtained were calculated. Combing resistance was measured using a Zwick type 1402 tensile tester (Zwick company, Einsingen uber Ulm/Donau, Federal Republic of Germany). The average work integral was based on the hairs treated with solution A (blank value). Accordingly, the reduction or increase in combing resistance may be derived from the following relation $$WC \text{ or } DC = \frac{\phi \text{ work integral test solution}}{\phi \text{ work integral solution A}} \times 100 \, [\%]$$

Accordingly, values under 100% represent a reduction and values over 100% an increase in the average combing resistance.

1.2 Result

The measurement data show that the addition of the polyaldehydocarboxylic acids POC-HS-2020 (average molecular weight 1400) and POC-HS-5060 (average molecular weight 4000) has only a slight effect upon the wet combability of test shampoo B, but considerably increases dry combing resistance.

The addition of the polyaldehydocarboxylic acid POC-HS-65120 (average molecular weight 8500) increases both wet and dry combing resistance. The addition of the polyaldehydocarboxylic acids and their salts reduces the smoothness of the dry hair.

2. APPLICATION EXAMPLES

2.1 Hair shampoo formulations

| | 2.1.1 | 2.1.2 | 2.1.3 | 2.1.4 | 2.1.5 | 2.1.6 |
|---|---|---|---|---|---|---|
| | \multicolumn{6}{c}{% by weight} | | | | | |
| $C_{12/14}$-fatty alcohol + 2 EO sulfate, Na salt, 28% (Texapon ® N25) | 50 | 35 | 50 | 50 | 60 | 40 |
| Octane-1-phosphonic acid | — | — | — | — | — | 1.0 |
| N—cocoalkylamidopropyl dimethyl glycine, 30% (Dehyton ® K) | 10 | — | — | — | — | 10 |
| Cocoamphoglycinate, 30% (Dehyton ® G) | — | 15 | — | — | — | — |
| N—cocoalkylamidopropyl dimethylamine oxide, 35% (Aminoxid WS 35) | — | — | 10 | — | — | — |
| Coconut oil fatty acid diethanolamide | 2 | 2 | 2 | 2 | 2 | 2 |
| Abietic acid-protein condensate (Lamepon ® PATR) | — | — | — | 5 | — | — |
| Ethylene glycol distearate | 2 | 2 | 2 | 2 | 2 | 2 |
| Polyaldehydocarboxylic acid, 40% (POC-HS-5060) | 5 | 5 | 5 | 5 | 5 | 6 |
| Triethanolamine to pH 6 | approx. 2 | approx. 2 | approx. 2 | approx. 2 | approx. 2 | approx. 3 |
| Water, perfume, dyes | ad 100 | ad 100 | ad 100 | ad 100 | ad 100 | ad 100 |

2.2 Hair rinse

| | |
|---|---|
| Polyaldehydocarboxylic acid, 40% (POC-HS-5060) | 2.0% by weight |
| Octyl phosphonic acid | 2.5% by weight |
| Hydroxyethyl cellulose | 1.2% by weight |
| Sodium hydroxide, 10% | to pH 4.5 |
| Water, perfume, dye | ad 100% |

2.3. Medicated hair gel

| | |
|---|---|
| Polyaldehydocarboxylic acid, 50% (POC-HS-2020) | 5.0% by weight |
| Cocoalkyl phosphate, Na salt, 15% (Forlanit ® F 452) | 3.0% by weight |
| Hydroxyethyl cellulose | 2.0% by weight |
| Triethanolamine | to pH 4.5 |
| Water, perfume, dye | ad 100% |

What is claimed is:
1. An aqueous composition for washing or rinsing hair consisting essentially of:
(A) an amount effective to reduce the smoothness of dry hair of at least one polyaldehydocarboxylic acid having an average molecular weight of from about 600 to about 10,000, containing from 5 to 9 carboxyl groups and correspondingly from 5 to 1 aldehyde groups per 10 monomer units, wherein the monomer units have the configuration $$-(CH_2-CH-)- \text{ and } -(CH_2-CH)- \\ \phantom{-(CH_2-}CHO \phantom{\text{ and } -(CH_2-}COOH$$

and non-toxic water-soluble addition salts thereof; and (B) from about 0.1 to about 10% by weight based on the total composition weight of an anionic hair-conditioning material which is at least one compound of the following formulae:

$RO(CH_2-CH_2-O)_nPO_3A_2$ $[RO(CH_2-CH_2-O)_n]_2PO_2A$ $RPO_3A_2$ $R-CH(OH)PO_3A_2$ $R-CX(PO_3A_2)_2$ in which R is a linear alkyl group containing from 8 to 18 carbon atoms; X is hydrogen, an —OH group or an —NH$_2$ group; A is an alkali metal, ammonium, mono-, di- or triethanolammonium cation; and n is 0 or an integer of from 1 to 12.

2. An aqueous composition in accordance with claim 1 wherein the at least one polyaldehydocarboxylic acid contains from 7 to 9 carboxyl groups per 10 monomer units.

3. An aqueous composition in accordance with claim 1 wherein the effective amount of the at least one polyadehydocarboxylic acid is from about 0.1 to about 10% by weight, based on the weight of the aqueous composition.

4. An aqueous composition in accordance with claim 1 wherein the aqueous composition includes from about 5 to about 50% by weight, based on the weight of the aqueous composition, of at least one anionic surfactant of the following formulae:

$R-SO_3-A$ $RO(CH_2-CH_2-O)_n-SO_3A$ in which R is a linear alkyl group having from 8 to 18 carbon atoms; A is an alkali metal, ammonium, or alkanol-ammonium cation; and n is 0 or an integer of from 1 to 12.

5. An aqueous composition in accordance with claim 1 wherein the aqueous composition includes from about 5 to about 50% by weight, based on the weight of the aqueous composition, of at least one anionic surfactant of the following formulae:

$R-SO_3-A$ $RO(CH_2-CH_2-O)_n-SO_3A$ in which R is a linear alkyl group having from 8 to 18 carbon atoms; A is an alkali metal, ammonium, or alkanol-ammonium cation; and n is an integer of from 1 to 12.

6. An aqueous composition in accordance with claim 5 wherein the anionic surfactant is the sodium salt of $C_{12}-C_{16}$-fatty alcohol polyglycol ether sulfate containing from 1 to 6 glycol ether groups.

7. An aqueous composition in accordance with claim 6 wherein from about 5 to about 20% by weight, based on the weight of aqueous composition, of said sodium salt is present.

8. An aqueous composition in accordance with claim 1 wherein the anionic hair-conditioning material is a water-soluble salt of at least one of the phosphoric acid monoester of a linear $C_{12}-C_{18}$ fatty alcohol; a phosphoric acid diester of a linear $C_{12}-C_{18}$-fatty alcohol; and a $C_8-C_{18}$-alkane-1-phosphonic acid.

9. In an aqueous shampoo or after-treatment rinse composition for washing or rinsing hair, the improvement comprising the presence therein of an amount effective to reduce the smoothness of dry hair of at least one polyaldehydocarboxylic acid having an average molecular weight of from about 600 to about 10,000, containing from 5 to 9 carboxyl groups and correspondingly from 5 to 1 aldehyde groups per 10 monomer units, wherein the monomer units have the configuration:

$$-(CH_2-CH-)- \text{ and } -(CH_2-CH)- \\ \phantom{-(CH_2-}CHO \phantom{\text{ and } -(CH_2-}COOH$$

or a non-toxic water-soluble addition salt thereof.

10. An aqueous solution in accordance with claim 1 wherein said effective amount is from about 0.1 to about 10% by weight, based on the weight of the aqueous composition.

* * * * *